United States Patent [19]

Hein et al.

[11] 4,093,108

[45] June 6, 1978

[54] SYRINGE ADAPTED TO OVERCOME A PRESSURE RESISTANCE

[75] Inventors: Wolfgang Hein, Dassel; Peter Grundmann, Konigswinter, both of Germany

[73] Assignee: Carl Schleicher & Schull, Einbeck, Germany

[21] Appl. No.: 750,427

[22] Filed: Dec. 14, 1976

Related U.S. Application Data

[63] Continuation of Ser. No. 594,633, Jul. 10, 1975, abandoned.

[30] Foreign Application Priority Data

Nov. 7, 1974 Germany ............................. 2433399

[51] Int. Cl.² ............................................. B65D 83/14
[52] U.S. Cl. ............................... 222/401; 73/425.4 P; 128/237
[58] Field of Search ................ 222/401, 402; 128/220, 128/237, 218 M; 141/27, 67; 73/425.4 P

[56] References Cited

U.S. PATENT DOCUMENTS

| | | | |
|---|---|---|---|
| 1,435,034 | 11/1922 | Ullman | 222/401 X |
| 1,623,101 | 4/1927 | Fisher | 222/401 X |
| 1,751,128 | 3/1930 | Cocks | 222/401 X |
| 3,635,218 | 1/1972 | Ericson | 128/220 X |
| 3,685,514 | 8/1972 | Cheney | 128/220 X |

*Primary Examiner*—Robert B. Reeves
*Assistant Examiner*—Francis J. Bartuska
*Attorney, Agent, or Firm*—Fulwider, Patton, Rieber, Lee & Utecht

[57] ABSTRACT

A syringe is adapted to overcome a pressure resistance at its outlet as may be provided, for instance, by a filter in communication with the outlet and through which the syringe is to pump a medium, particularly a liquid medium, for filtration. The syringe comprises a first cylinder containing a piston and a piston rod. The piston rod is fixed to a second piston sliding within a longitudinal bore in the first-mentioned piston. The bore and the second piston cooperate to define an air-filled pressure chamber connected to a first cylinder chamber, defined by the first piston and the first cylinder, by a valve. Inward movement of the piston rod produces an over-pressure (e.g. 16 atmospheres) in the pressure chamber to open the valve to apply the over-pressure to the liquid or other medium in the cylinder chamber to overcome the pressure resistance of the filter and enable the liquid to be forced through the filter.

2 Claims, 4 Drawing Figures

A

B

C

SYRINGE ADAPTED TO OVERCOME A PRESSURE RESISTANCE

CROSS-REFERENCE TO RELATED APPLICATION

This application is a continuation of U.S. Ser. No. 594,633, filed July 10, 1975, now abandoned and entitled SYRINGE ADAPTED TO OVERCOME A PRESSURE RESISTANCE.

BACKGROUND OF THE INVENTION

1. Field of the Invention

The invention relates to a syringe comprising a cylinder, a piston rod and a piston disposed for displacement within the cylinder by displacement of the piston rod, whereby when the piston rod is displaced in one direction a medium is drawn into the interior of the cylinder while when the rod is displaced in the opposite direction the medium is expelled from the cylinder.

2. Description of the Prior Art

Such syringes are used, for example, for forcing media through filters. In this case, a filter assembly disposed in a filter holder may be connected to the outlet of the syringe. Such arrangements are used, for example, for the cleaning or sterile filtration of small quantities of liquid. In order, then, to propel the liquid, for example in a quantity of 1 to 50 ml, through the filter assembly which is connected to the syringe, a high pressure is required which has to be generated by hand. In the case of known syringes, the liquid or other medium to be filtered is forced through the filter assembly by an inward movement of the piston rod and thus an inward movement of the piston disposed in the cylinder. Under such circumstances, the hand must apply considerable force. In the case of very dense filter materials or where several filter materials are connected in series, particularly diaphragm filters, filtration in this manner is impossible.

SUMMARY OF THE INVENTION

An object of the invention is to provide a syringe with which it is possible to overcome pressure resistance as might be afforded by filter means.

This object is achieved in that there is provided in the interior of a first piston in a first cylinder a pressure chamber having a cross section which is reduced in size with respect to the cylinder first cross section. Upon inward movement of the piston rod, an over-pressure is created in the pressure chamber. When there is an over-pressure, the pressure chamber can be connected to the cylinder chamber in which is disposed the medium which is to be expelled, the connection being made by a connecting device having shut-off means. The over-pressure forces the medium out of the syringe against any pressure resistance.

The pressure chamber is disposed in the interior of the cylinder and the pressurizable medium disposed therein may be air. A simple construction is possible if the pressure chamber is constructed as a duct extending in the direction of displacement of the piston rod, the piston rod being guided in the duct. Furthermore, that end of the piston rod which is disposed in the interior of the first piston may be provided with a second piston which is displaceable in the duct and which forms one end of the pressure chamber, the connecting device with the shut-off means being disposed at the other end limit of the pressure chamber.

This connecting device with the shut-off means can be a valve which is opened as a result of over-pressure in the pressure chamber. As a result, the over-pressure produced in the pressure chamber by the depression of the piston rod is applied to the medium to be expelled from and disposed in the cylinder chamber in front of the first piston.

Furthermore, the second piston which is displaceable in the interior of the first piston can be provided with a valve. The piston rod can be alternately moved into and out of the second cylinder formed in the first piston, exerting a pumping action on the medium which is to be expelled, so that by reason of this pumping action, the medium can be forced through the filter arrangement or overcome some other pressure resistance.

In order to guarantee a functionally-correct opening and closing of the valves, the valve closure elements can be biased by adjustable spring forces as is apparent to those skilled in the art.

An important advantage of the invention resides particularly in the fact that it is possible, by applying a small amount of force, to overcome for example a high difference in pressure obtaining in a filter assembly. Thus, in the case of very dense filter materials or in the case of multiple filter materials disposed one after another, particularly diaphragm filters, a filtration operation can be performed which was not hitherto possible with a syringe. By repeated reciprocating movement of the piston rod and by reason of the pumping action exerted thereby on the medium to be expelled, it is possible to eliminate from the interior of the cylinder all the liquid which is to be filtered, the liquid being forced out through the filter arrangement. Also, it is possible by means of the invention to expel finely adjusted doseages from the cylinder.

The device according to the invention is extremely versatile in application. For example, it can be used for the sterile filtration of pharmaceutical liquids such as for example eye drops or parenteral solutions. Furthermore, it can be used for example in homeopathic dispensing. The invention can also be used to advantage in the preparation and sterile filtration of water, particularly drinking water. In addition, it can be used for filtering off particulate impurities of all kinds from liquids, particularly rinsing liquids, for example in the electronics industry, in the manufacture of miniaturized transistor parts, photo varnishes and the like. It is also possible to apply the invention to clinical purposes, particularly in the case of injection syringes.

Furthermore, the syringe according to the invention can be used as a normally acting or regular syringe, i.e., by withdrawing the piston, a liquid medium can be drawn into the interior of the cylinder after which, by moving the piston rod together with the piston and the valve arrangement disposed therein back into the cylinder, it is possible to expel from the cylinder the liquid which is to be filtered. This use is then the same as with conventional syringe devices.

BRIEF DESCRIPTION OF THE DRAWINGS

The invention will be explained in greater detail hereinafter with reference to a preferred syringe shown in the accompanying drawings, in which.

DESCRIPTION OF THE PREFERRED EMBODIMENT

Figure 1:
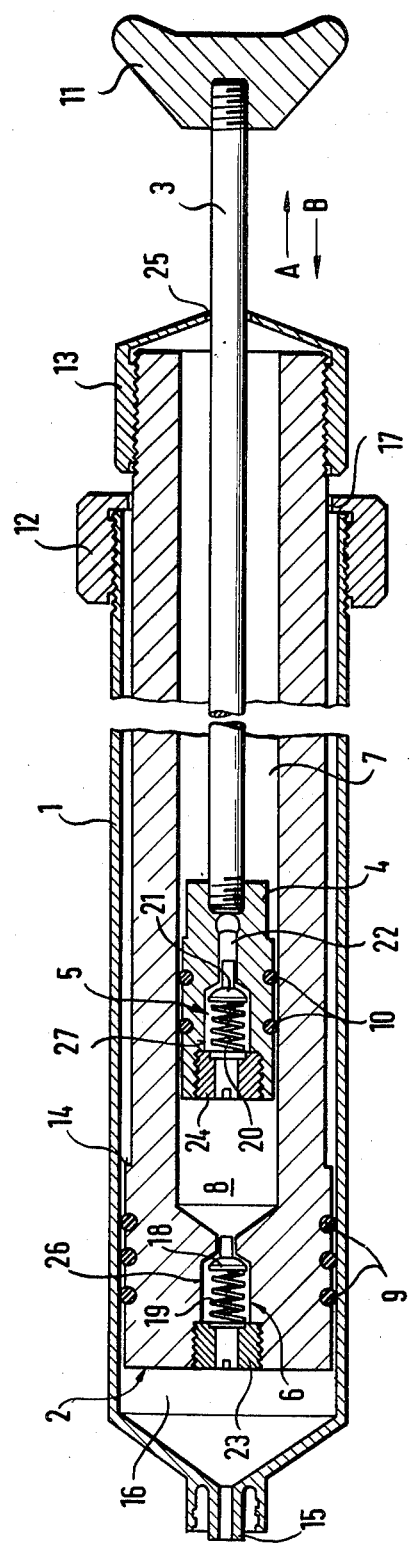
FIG. 1 is a longitudinal section through syringe.

The illustrated syringe comprises a first cylinder or barrel 1 in which there is displaceably arranged a first piston 2 having a concentric extension 7' of reduced diameter at one end thereof serving as a piston rod. A piston rod 3 serves to move the first piston 2. In the interior of the first piston 2 there is arranged a second piston 4 which can be displaced by means of the piston rod 3. The pistons 2 and 4 are provided with respective valves 5 and 6 at their ends which are nearer the outlet from the syringe.

The second piston 4 is disposed for displacement within the first piston 2 in a longitudinal bore 7 forming a second cylinder in the first piston 2. On the side of the second piston 4 at which the valve 5 is disposed there is a pressure chamber 8 which lies between the two valves 5 and 6.

Sealing rings 9 are provided to seal off the piston 2 with respect to the wall of the first cylinder 1. Sealing rings 10 are provided to seal off the second piston 4 with respect to the wall of the longitudinal bore 7.

For actuation of the piston rod 3, the rod is provided with a handle 11. At its closed end, i.e., the end remote from its outlet, the first cylinder is provided with a cylinder cover 12 in which there is an aperture 17 through which the reduced diameter extension 7' of first piston 2 is guided. The longitudinal bore 7 within the first piston 2 is closed at its end remote from the second cylinder outlet by means of a piston cover 13. The first piston 2 is further provided with a stop 14 formed as a shoulder. Within a cylinder chamber 16 defined by the part of the cylinder 1 between the first piston 2 and the cylinder outlet, which is provided with a cylinder attachment 15, is a liquid or other medium which is, for example, to be filtered, or which is to be removed from the cylinder by the action of the pressure of a pressure device within the cylinder 1. It is possible to mount on the cylinder attachment 15 a filtering arrangement (not shown) which may take the form of a filter holder.

The valve 6 comprises a valve closure element 18 and a spring 19; and is disposed in a bore 26 within the first piston 2. The valve 5 comprises likewise a valve closure element 21 and a spring 20, and is disposed in a bore 27 within the piston 4. The springs 19 and 20 press the closure elements 18 and 21 respectively into valve-closing positions.

A pressure medium for the pressure chamber 8 is air which can pass through an inlet duct 22 having a radial portion 22' through the open valve 5 into the pressure chamber 8.

Figure 2:
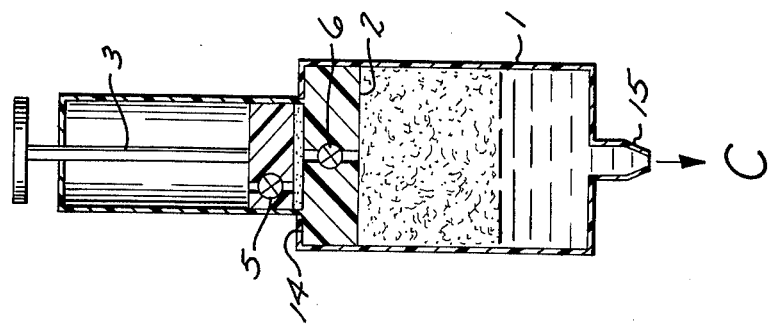
FIGS. 2A, 2B and 2C illustrate diagrammatically several positions of the cooperating elements during operation of the invention.
Figure 2:
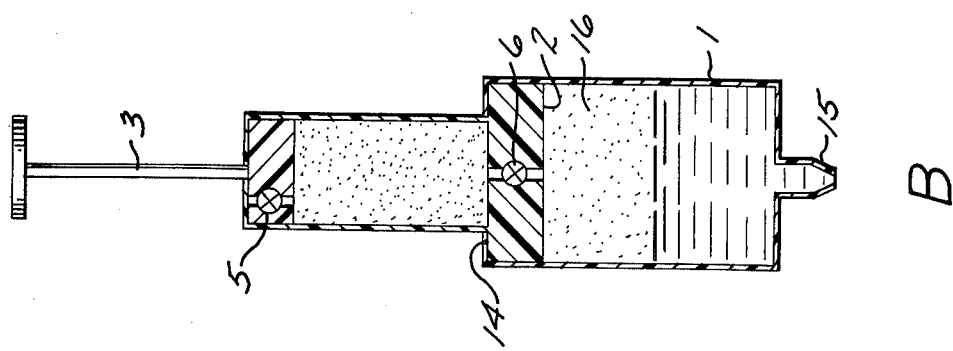
Figure 2:
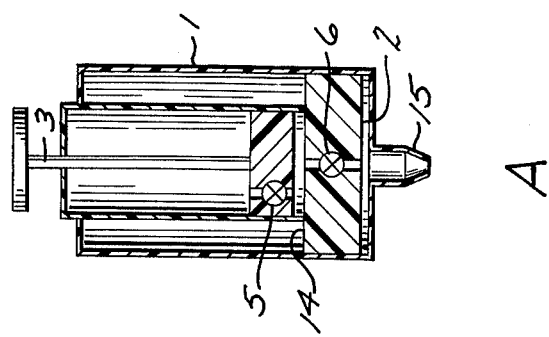

The illustrated syringe operates in the following manner:

Starting from a normal position of the device as depicted in FIG. 2A, the piston rod 3 is drawn outwardly of the cylinder 1 in the direction of the arrow A which displaces the piston 2 within the cylinder 1, when the valves 5 and 6 are closed, in the direction of the arrow A. This displacement takes place until such time as the stop 14 on the first piston abuts the cylinder cover 12. When this happens, for example, a liquid which is to be filtered is drawn into the cylinder chamber 16 through the aperture in the cylinder attachment 15 (FIG. 2B). The piston 2 is displaced thereby through the aperture 17 in the cylinder cover 12.

As the liquid is drawn into the cylinder chamber 16, a pumping action generated by means of the second piston 4 displaceable in the longitudinal bore 7, is used. This pumping action occurs during the reciprocating movement of the piston rod 3 and that of the second piston 4.

As the piston rod 3 is moved in the direction of the arrow A, a negative pressure is created within the pressure chamber 8, whereby by reason of the force of the spring 19, the valve 6 remains closed so that no liquid can pass out of the cylinder chamber 16 into the pressure chamber 8. By reasons of the pressure difference obtaining on both sides of the closure element 21 of the valve 5, mainly by reason of the pressure difference between atmospheric pressure and the negative pressure in the pressure chamber 8, the closure element 21 is displaced against the force of the spring 20 so that the valve 5 is opened. The outside air can then flow through the gap at rod aperture 25 through bore 7, radial aperture 22', duct 22 and through valve 5, and then into the pressure chamber 8 until more or less atmospheric pressure obtains in the pressure chamber 8.

The piston rod 3 is then moved in the direction of the arrow B. This movement produces in the pressure chamber 8 an over-pressure so that the closure element 18 is displaced against the force of the spring 19 into its open position, so that the valve 6 in the piston 2 is opened. The pressure chamber 8 is then in communication with the cylinder chamber 16 upstream of the piston 2 in which is the liquid which is to be ejected. Upon further movement of the piston rod 3, then, the liquid disposed in the cylinder chamber 16 is forced through the aperture in the cylinder attachment 15 against the pressure resistance or back pressure built up, for example, by a filter arrangement (FIG. 2C). As a result of the over-pressure in the pressure chamber 8, which acts on the liquid to be expelled, this pressure resistance is overcome. By means of the device illustrated, it is readily possible to achieve an over-pressure of 15 atm above atmosphere. After the piston 4 has been pressed all the way into the longitudinal bore 7, the piston 4 is, by actuation of the piston rod 3, withdrawn again in the direction of the arrow A, so that the aforedescribed cycle is repeated. By virtue of this pump movement being repeated several times, it is possible for the cylinder chamber 16 to be completely emptied. It is also possible during the pumping movement to achieve accurate dispensing. The forces of the springs 19 and 20 in the two valve chambers of the valves 5 and 6 can be regulated by adjusting screws 24 and 23. The spring forces are selected as a function of the desired pressure which it is intended to apply upon expulsion of the liquid from the cylinder chamber 16. Accordingly, so it is naturally also possible to adjust the over-pressures to a value less than 15 atm above atmospheric, whereby the same amount of force is always required when expelling the liquid which is to be filtered.

The cylinder 1 and the piston 2 can be made from synthetic plastics material. If it is required by the nature of the application to which the syringe is to be put, they can be of a physiologically sterile material.

The arrangement illustrated can also be used as a quite conventional syringe in that the liquid disposed in the cylinder chamber 16 can be forced out by inward movement of the piston 2.

Obviously, many modifications and variations of the present invention may be made with regard to the foregoing detailed description without departing from the spirit of the invention.

We claim:

1. A syringe for expelling a liquid medium for filtration, said syringe comprising:
   a first cylinder cooperating with a first piston having a first hollow piston rod and defining a first pressure chamber, the hollow portion of said hollow piston rod defining a second cylinder having a smaller cross section than said first cylinder and cooperating with a second piston having a second piston rod and defining in said second cylinder a second pressure chamber;
   a bore formed within said first piston connecting said first and second pressure chambers;
   a valve in said bore having a valve closure element and means biasing said valve closure element to open the valve upon an over-pressure in said second pressure chamber;
   an inlet/outlet attachment for the liquid medium opening into said first pressure chamber;
   an air inlet duct formed in said second piston opening into said second pressure chamber;
   a second valve that opens in response to an under-pressure in said second pressure chamber during an air intake stroke of said second piston and closes in response to an air over-pressure in said second pressure chamber during an air pressurizing stroke of said second piston, said second valve being in communication with said air inlet duct;
   a cover for said first cylinder;
   a stop on said first piston which is able to abut said cover in the extreme intake stroke position of the first piston; and
   with said liquid medium charged into said first pressure chamber by means of an intake stroke of the first piston being expelled by means of an air over-pressure provided upon said liquid medium within said first pressure chamber by means of a pumping action of said second piston.

2. A syringe according to claim 1, wherein said means for biasing said valve closure element is provided with an adjustable spring force.

* * * * *